US005637570A

United States Patent [19]
Arora et al.

[11] Patent Number: 5,637,570
[45] Date of Patent: Jun. 10, 1997

[54] DISUBSTITUTED AND TRISUBSTITUTED DERIVATIVES OF 2,3:4,6-DI-O-ISOPROPYLIDENE-α-L-XYLO-2-HEXULOFURANOSONIC ACID HAVING ANTI-CANCER, ANTI-INFLAMMATORY AND ANTI-PROLIFERATIVE ACTIVITY

[75] Inventors: Sudershan K. Arora, Derry, N.H.; Manoj K. Gupta, Mathana, India; Pushappam Lukos, Mathana, India; Ravinder Kumar, Mathana, India; Shanti N. Sawhney, Mathana, India

[73] Assignee: Chemora Pharmochem, Derry, N.H.

[21] Appl. No.: 437,378

[22] Filed: May 9, 1995

[51] Int. Cl.$^6$ .......................... A61K 31/70; C07H 15/00
[52] U.S. Cl. .................. 514/25; 514/23; 536/4.1; 536/17.6; 536/17.9
[58] Field of Search .................. 536/4.1, 17.6, 536/17.9; 514/23, 25

[56] References Cited

U.S. PATENT DOCUMENTS 5,010,058  4/1991  Ronsen et al. ............... 514/23

*Primary Examiner*—Elli Peselev
*Attorney, Agent, or Firm*—Oblon, Spivak, McClelland, Maier & Neustadt, P.C.

[57] ABSTRACT

Novel disubstituted and trisubstituted derivatives of 2,3:4,6-di-O-isopropylidene-α-L-xylo-2-hexulofuranosonic acid containing at least one alkyl group at position 1, position 4 being occupied by OH, O-alkylamino or O-alkylaminoheterocyclic moiety, and the OH group at position 6 being replaced by a saturated heterocyclic moiety or aminoalkyl heterocyclic group. These compounds exhibit anti-cancer, anti-inflammatory and/or anti-proliferative activities. Methods of preparation, pharmaceutical compositions containing the compounds and methods of treating cancer, inflammatory and/or autoimmune disorders employing the compounds are described.

10 Claims, No Drawings

DISUBSTITUTED AND TRISUBSTITUTED DERIVATIVES OF 2,3:4,6-DI-O-ISOPROPYLIDENE-α-L-XYLO-2-HEXULOFURANOSONIC ACID HAVING ANTI-CANCER, ANTI-INFLAMMATORY AND ANTI-PROLIFERATIVE ACTIVITY

BACKGROUND OF THE INVENTION

I. Field of the Invention

The present application relates to a group of disubstituted and trisubstituted α-L-xylo-2-hexulofuranoses not previously disclosed, and having anti-inflammatory and antiproliferative properties to a degree far exceeding those of previously described compounds as well as having a greatly protracted effect as compared with previously described compounds.

More specifically, the present invention relates to 2,3-O-isopropylidene-1-O-alkyl or substituted alkyl or arylalkoxyalkyl-6-deoxy-6-amino or 6-deoxy-6-thio alkyl- or substituted alkyl- or aralkyl or saturated heterocycle or saturated heterocyclic alkyl-α-L-xylo-2-hexulofuranoses and their preparation. This invention further relates to 6-deoxy-2,3-O-isopropylidene-1,4-disubstituted-α-L-xylo-2-hexulofuranoses and their preparation. This invention further relates to 6-deoxy-2,3-O-isopropylidene-1,4,6-trisubstituted-α-L-xylo-2-hexulofuranoses and their preparation. The compounds of the present invention have shown significant anti-cancer, anti-inflammatory, and antiproliferative activity and are useful for treating warm blooded animals and mammals with various cancer diseases (such as Melanoma, Leukemia, cancers of Lung, Colon, CNS, Breast, Prostrate etc.), rheumatoid arthritis, osteoarthritis, scleroderma, systemic lupus erythmatosus, autoimmune deficiency syndrome, atopic dermatitis, asthma, and psoriasis among others. Therefore, this invention also relates to pharmaceutical compositions containing the compounds of the present invention and methods of treating cancer, inflammatory and/or autoimmune disorders.

DESCRIPTION OF THE RELATED ART

Isopropylidene and benzylidene groups are the most commonly used protective groups in carbohydrate chemistry. These groups are introduced into a molecule under similar conditions; however, the location of the protection can be quite different. The reason for this difference is directly related to the stability of each protected molecule. Since protection normally occurs under conditions which allow reversibility, reaction proceeds until equilibrium is reached. The distribution of products at equilibrium is determined by their relative thermodynamic stabilities. In other words, these reactions are thermodynamically controlled. Benzylidene groups prefer to be part of six-membered ring acetals, while the ketals resulting from acetonation generally are 5-membered rings. The difference is attributed to the effect of the methyl and phenyl substituents on the stability of the particular ring systems. These blocking methods are described in U.S. Pat. Nos. 2,715,121, 4,056,322, 4,735,934, 4,996,195, and 5,010,058 the disclosures of which are incorporated herein by reference. Other blocking methods are also described in J. Carbohydr. Chem., 4, 227 (1985); 3, 331 (1984); Methods in Carbohydr. Chem., 1, 191 (1962); 1, 107 (1962); Can. J. Chem., 62, 2728 (1984); 47, 1195, 1455 (1969); 48, 1754 (1970) all incorporated herein by reference. Literature reveals that in the case of D-glucose, which is blocked in its furanose ring structure, the 1,2-, and 5,6-hydroxyl groups can be blocked using an isopropylidene blocking group with the 3-position left open to undergo derivatization. The therapeutic activity of hexoses and their derivatives are also disclosed in some of the above applications.

A majority of the compounds of the present invention have been screened by the National Cancer Institute for various in vitro cancer cell lines belonging to Melanoma, Leukemia, cancers of Colon, CNS, Prostrate, Breast etc. and have shown significant activity. Two compounds were also tested in in vivo cancer models. To the inventor's knowledge there is no example available in the literature wherein derivatives of monosaccharides are being used to treat various cancer patients. While some of the prior art hexose derivatives have shown beneficial therapeutic activity, high doses of these compounds, such as Amiprilose.HCl, are often needed to be effective and produce the desired results. Therefore, such prior art derivatives are difficult to prescribe orally. Because therapy for those inflammatory and autoimmune disorders is often midterm and longterm, there is a need to develop potent, non-toxic compounds which can be orally administered to promote ease of treatment and patient compliance.

OBJECTS OF THE INVENTION

An object of the present invention, therefore, is to provide a new class of compounds (hexulofuranose derivatives) that exhibit significantly greater potency than available compounds in order to provide ease of treatment, particularly oral administration. It is believed that the compounds of the present invention act by a different mechanism than Amiprilose.HCl and are more selective in their activity.

In U.S. Pat. Nos. 5,360,790 and 5,367,062 α-D-mannofuranosides and α-D lyxofuranosides were used as a core nucleus. However, in the present application it has been discovered that replacement of the nucleus from α-D-mannofuranoside or lyxofuranoside by α-L-xylo-2-hexulofuranose increases the activity tremendously in various pharmacological assays. It appears that L-hexoses coupled with substitution at the 1-position (preferably alkyl) and another substitution at 5- and/or 6-position (preferably o-heterocyclic alkyl, heterocyclic alkyl, N-heterocycle, N-heterocyclic alkyl, etc.) plays an important role for displaying significant activity in combatting various diseases including cancer. The biological data obtained so for clearly indicate that L-hexoses and O-substitution at the 1-position (as described in the present application) is preferred over O-glycosidic substitution as described U.S. Pat. Nos. 5,360, 790 and 5,367,062 both incorporated herein by reference.

Another object of the present invention is to provide novel carbohydrate compounds (hexulofuranose derivatives) that exhibit significantly greater potency for cancer treatment. There is no example available in the literature wherein α-L-xylo-2-hexulofuranose derivatives or any other monosaccharides are used as a therapy for treating cancer patients.

It is a further object of this invention to provide novel compounds that exhibit significantly increased potency over available compounds, such as Therafectin (Amiprilose.HCl), in order to provide ease of oral administration.

Other objects and advantages of the invention will be forth in the description which follows, and in part will be apparent from the description, or may be learned by practice of the invention. The objects and advantages of the invention may be realized and obtained by means of the compounds, pharmaceutical compositions and methods of treatment pointed out in the appended claims.

SUMMARY OF THE INVENTION

In order to achieve the above-mentioned objects and in accordance with the purpose of the invention as embodied and broadly described herein there is provided i) an α-L-xylo-2-hexulofuranose having the following general formula:

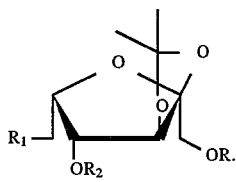

In compounds of the formula
R is $C_{10}$–$C_{15}$ alkyl;

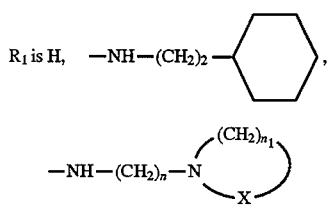

wherein x is O or $CH_2$ and n and $n_1$ are from 2–6 or

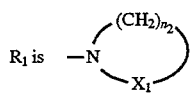

wherein $X_1$ is O or $CH_2$ and $n_2$ is 2–6;

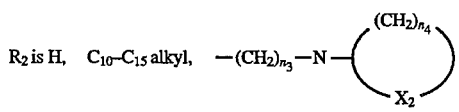

wherein $X_2$ is O or $CH_2$ and $n_3$ and $n_4$ are from 2–6, or $R_2$ is —$(CH_2)_{n5}$—$N(CH_3)_2$ wherein $n_5$ is from 2–4.

Preferred compounds are those where $R_1$ and $R_2$ are not H at the same time. Acid addition salts of the above compounds are also included in the invention.

The present invention also provides pharmaceutical compositions for the treatment of cancer, inflammatory and/or autoimmune disorders. These compositions comprise an effective amount of at least one of the above compounds and/or an effective amount of at least one physiologically acceptable acid-addiction salt thereof, with a pharmaceutically acceptable carrier.

The α-L-xylo-2-hexulofuranose compounds of the present invention exhibit greater potency in terms of their activity (Con-A, Fibroblast, Mixed Lymphocyte Response, and cancer cell lines), than known glucofuranose compounds, such as THERAFECTIN (Amiprilose.HCL). These novel compounds have been demonstrated in vitro to decrease skin cell proliferation and inhibition of the proliferative response of spelenic T-lymphocytes to known mitogen. Since T-lymphocytes are the immune cells that regulate immune responses the compounds of the present invention are usefull for treating warm blooded animals and mammals with inflammatory and/or autoimmune disorders such as rheumatoid arthritis, osteoarthritis, psoriasis, atopic dermatitis, scleroderma, systemic lupus erythematosus, and autoimmune deficiency syndrome (ARC, AIDS, etc.). The present compounds also have demonstrated anti-cancer activity in various cancer cell lines using various in vitro assays as well as in vivo models. Also, the compounds of the present invention can be administered internally or externally.

DETAILED DESCRIPTION OF THE INVENTION

The compounds of the present invention may be prepared by techniques well known in the art and familiar to the average synthetic organic chemist. In addition, the invention compounds may be prepared by the following reaction sequences which also show preferred R, $R_1$ and $R_2$ groups:

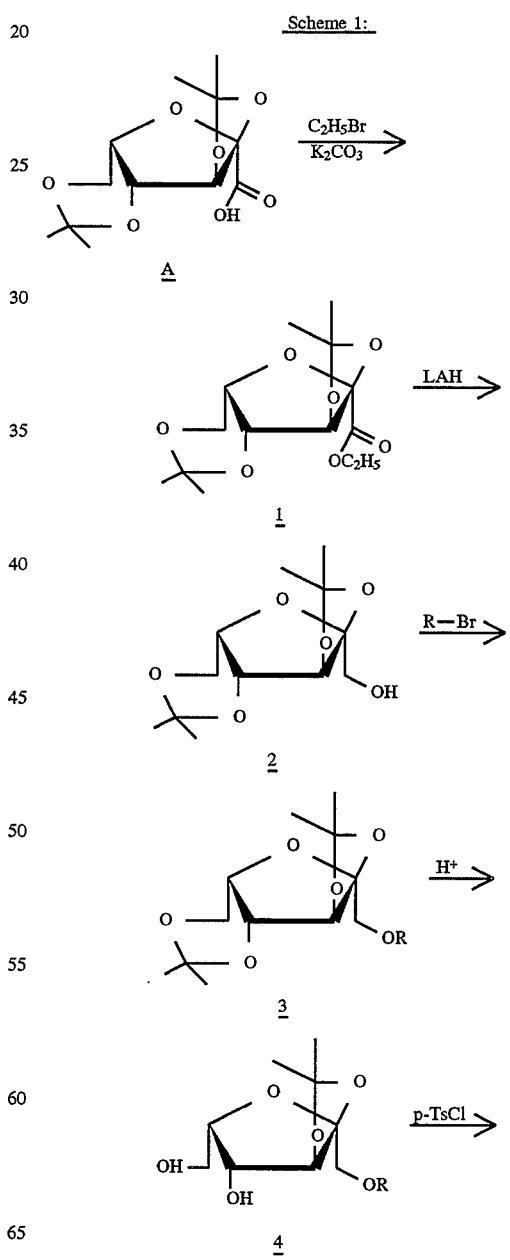

Scheme 1:
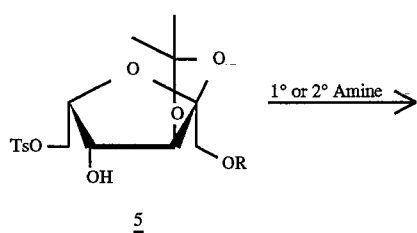
5
1° or 2° Amine →
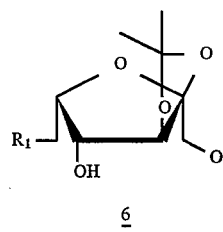
6
Wherein R is C₁₂H₂₅:
R₁ is 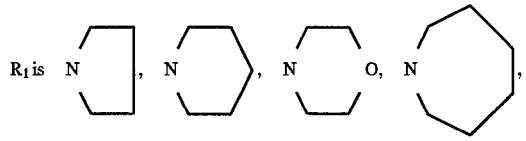
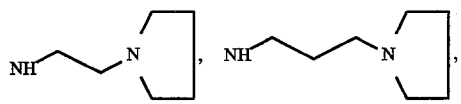,
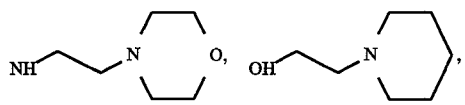,
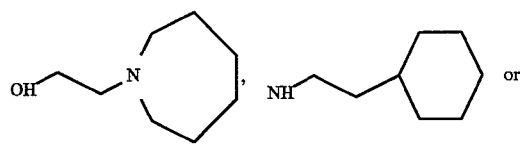
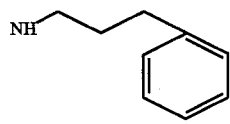
Scheme 2:
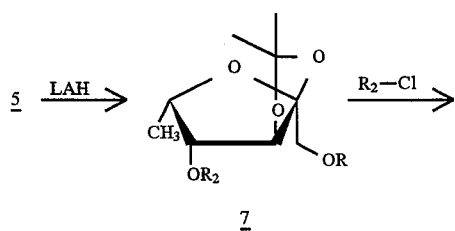
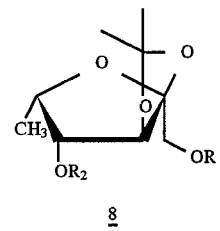
8
Wherein R is C₁₂H₂₅:
R₂ is 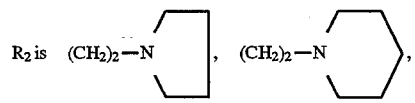,
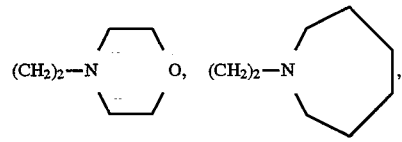,
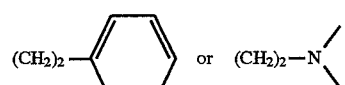
Scheme 3:
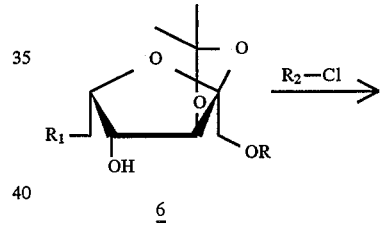
6
R₂—Cl →
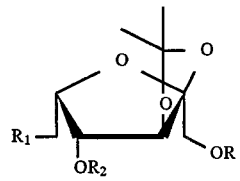
9
R = C₁₂H₂₅
R₁ = 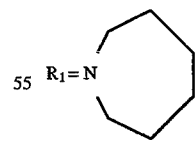
R₂ is 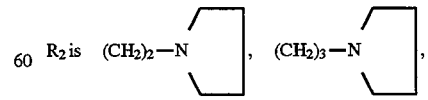,
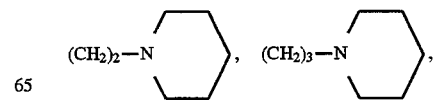, -continued
Scheme 3:

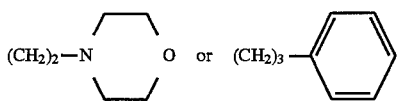

In scheme 1, 2,3:4,6-di-O-isopropylidene-α-L-xylo-2-hexulofuranose (2) was prepared by treating 2,3:4,6-di-O-isopropylidene-α-L-xylo-2-hexulofuranosonic acid A (commercially available compound) with ethyl bromide in the presence of potassium carbonate followed by the reduction of the ester obtained with lithium aluminium hydride. The free OH group at 1-position of compound 2 is then treated with alkyl halide in the presence of powdered sodium hydroxide. This reaction was carried out in an oil bath at 80°–120° C. Alternatively, the reaction was also carried out in a domestic microwave oven at a medium power with a sufficient reduction in the reaction time. The compound 3 so obtained is hydrolyzed with 30% aqueous perchloric acid to afford 2,3-O-isopropylidene-1-O-alkyl-α-L-xylo-2-hexulofuranose (4) which is selectively tosylated at 6-position to compound 5. This compound is then treated with the desired amine (primary or secondary) at 70°–90° C. in an oil bath or heated in a microwave oven operating at 50% power.

The compounds of scheme 2 are obtained by treating compound 5 with $LiAlH_4$ to compound 7 followed by reaction with a suitable halide to afford compounds of formula 8.

In scheme 3, the free —OH group of compound 6 (R is $C_{12}H_{25}$ and $R_1$ is hexamethyleneimino) is treated with powdered sodium hydroxide and appropriate halide to afford trisubstituted compounds of formula 9. The reaction is carried out in an oil bath or in microwave oven at 50% power.

In the above synthesis, where specific bases, acids, etc. are mentioned, it is to be understood that other acids, bases, etc. may be used. Similarly, the power and time of microwave heating may be adjusted according to the desired results.

Preferred compounds according to the invention and capable of being produced by Scheme 1 include:
Ia. 2,3-O-Isopropylidene-6-deoxy-6-(1-pyrrolidinyl)-1-O-dodecyl-α-L-xylo-2-hexulofuranose
Ib. 2,3-O-Isopropylidene-6-deoxy-6-(1-piperidinyl)-1-O-dodecyl-α-L-xylo-2-hexulofuranose
Ic. 2,3-O-Isopropylidene-6-deoxy-6-(1-morpholinyl)-1-O-dodecyl-α-L-xylo-2-hexulofuranose
Id. 2,3-O-Isopropylidene-6-deoxy-6-(1-hexamethyleneimino)-1-O-dodecyl-α-L-xylo-2-hexulofuranose
Ie. 2,3-O-Isopropylidene-6-deoxy-6-aminoethylpyrrolidinyl)-1-O-dodecyl-α-L-xylo-2-hexulofuranose
If. 2,3-O-Isopropylidene-6-deoxy-6-aminoethylmorpholinyl-1-O-dodecyl-α-L-xylo-2-hexulofuranose
Ig. 2,3-O-Isopropylidene-6-deoxy-6-aminoethylpiperidinyl-1-O-dodecyl-α-L-xylo-2-hexulofuranose
Ih. 2,3-O-Isopropylidene-6-deoxy-6-aminoethylhexamethyleneimino-1-O-dodecyl-α-L-xylo-2-hexulofuranose
Ii. 2,3-O-Isopropylidene-6-deoxy-6-aminopropylpyrrolidinyl-1-O-dodecyl-α-L-xylo-2-hexulofuranose
Ij. 2,3-O-Isopropylidene-6-deoxy-6-aminoethylcyclohexyl-1-O-dodecyl-α-L-xylo-2-hexulofuranose
Ik. 2,3-O-Isopropylidene-6-deoxy-6-phenylpropylamino-1-O-dodecyl-α-L-xylo-2-hexulofuranose Further preferred compounds according to the invention and capable of being produced by scheme 2 include:
Il. 2,3-O-Isopropylidene-6-deoxy-1-O-dodecyl-4-O-ethylpyrrolidinyl-α-L-xylo-2-hexulofuranose
Im. 2,3-O-Isopropylidene-6-deoxy-1-O-dodecyl-4-O-ethylpiperidinyl-α-L-xylo-2-hexulofuranose
In. 2,3-O-Isopropylidene-6-deoxy-1-O-dodecyl-4-O-ethylmorpholinyl-α-L-xylo-2-hexulofuranose
Io. 2,3-O-Isopropylidene-6-deoxy-1-O-dodecyl-4-O-ethylhexamethyleneimino-α-L-xylo-2-hexulofuranose
Ip. 2,3-O-Isopropylidene-6-deoxy-1-O-dodecyl-4-O-phenylpropyl-α-L-xylo-2-hexulofuranose
Iq. 2,3-O-Isopropylidene-6-deoxy-1-O-dodecyl-4-O-3'-(N',N'-dimethylaminopropyl)-α-L-xylo-2-hexulofuranose Further preferred compounds of the invention and capable of being produced by scheme 3 include:
Ir. 2,3-O-Isopropylidene-6-deoxy-1-O-dodecyl-4-O-ethylpyrrolidinyl-6-hexamethyleneimino-α-L-xylo-2-hexulofuranose
Is. 2,3-O-Isopropylidene-6-deoxy-1-O-dodecyl-4-O-propylpyrrolidinyl-6-hexamethyleneimino-α-L-xylo-2-hexulofuranose
It. 2,3-O-Isopropylidene-6-deoxy-1-O-dodecyl-4-O-ethylpiperidinyl-6-hexamethyleneimino-α-L-xylo-2-hexulofuranose
Iu. 2,3-O-Isopropylidene-6-deoxy-1-O-dodecyl-4-O-propylpiperidinyl-6-hexamethyleneimino-α-L-xylo-2-hexulofuranose
Iv. 2,3-O-Isopropylidene-6-deoxy-1-O-dodecyl-4-O-ethylmorpholinyl-6-hexamethyleneimino-α-L-xylo-2-hexulofuranose
Iw. 2,3-O-Isopropylidene-6-deoxy-1-O-dodecyl-4-O-phenylpropyl-6-hexamethyleneimino-α-L-xylo-2-hexulofuranose
Ix. 2,3-O-Isopropylidene-6-deoxy-1-O-dodecyl-4-O-3'-(N',N'-dimethylaminopropyl)-6-hexamethyleneimino-α-L-xylo-2-hexulofuranose The disubstituted and trisubstituted derivatives of α-L-xylo-2-hexulofuranose of the present invention exhibit various pharmacological properties and are, therefore, useful for treating animals and mammals with various cancer diseases as well as inflammatory and/or autoimmune disorders.

The free amino compounds of the invention are basic and form organic and inorganic acid salts. The resulting salts are useful by themselves, and in the therapeutic composition and method of invention, etc. These salts may be prepared by the usual prior art techniques, such as suspending the compound in water and then adding one equivalent of the desired organic acid or mineral acid. Examples of suitable acids include HCl, $H_2SO_4$, $HNO_3$, maleic acid, benzoic acid, tartaric acid, acetic acid, p-aminobenzoic acid, oxalic acid, succinic acid, and glucoronic acid. The neutral solution of the resulting salt is subjected to rotary evaporation under diminished pressure to the volume necessary to assure precipitation of the salt upon cooling, which is then filtered and dried. The salts of the present invention may also be prepared strictly under non-aqueous conditions, for example, dissolving the free amine in ether and adding exactly one equivalent of the desired acid in ether. Stirring the solution at 0°–5° C. causes the precipitation of the amine salt which are filtered, washed with ether and dried. The amine salts are often preferred for use in formulating the therapeutic compositions of the invention as they are crystalline and relatively more stable and non-hygroscopic. The amine salts are also better adapted for intramuscular injection than are the free amines.

Because of their valuable pharmacological properties, the compounds of the present invention may be administered to a human patient or an animal to be treated either orally, topically, rectally, internasally or by parenteral administration. When the therapeutic composition is to be administered orally, it is preferred that the compounds of the present invention be admixed with a prior art filler and/or binder such as starch and a disintegrator, and the admixture pressed into a tablet of a size convenient for oral administration. Capsules also may be filled with the powdered therapeutic composition and administered orally. Alternatively, a water solution of the amine salt or suspension of the therapeutic composition may be admixed with a flavored syrup and administered orally. A salt of the free amine is usually preferred where the compound is administered by intramuscular injection.

The pharmaceutical compositions of the invention are preferably produced and administered in dosage units, each unit containing as active component a certain amount of at least one compound of the present invention and/or at least one physiologically acceptable acid addition salt thereof. The dosage may be varied over extremely wide limits as the compounds are effective at low dosage levels and are relatively free of toxicity. The compounds may be administered in the minimum quantity which is therapeutically effective, and the dosage may be increased as desired up to the maximum dosage tolerated by the patient. In the case of an animal or human, the effective dose to treat disorders including autoimmune and or anti-inflammatory disorders can range from about 1 to 50 mg per kilogram of body weight per day, preferably about 2–30 mg per kilogram per day, over a period required for treatment. In the case of in vitro testing, the effective amount to achieve 50% inhibition of cultured cells range from 1–100 µg per ml of the cultured medium, preferably 2–50 µg per ml.

Several compounds representative of those described above were evaluated in vitro against a total of 56–60 human tumor cell lines derived from nine cancer types (leukemia, non-small cell lung cancer, colon cancer, CNS cancer, melanoma, ovarian cancer, renal cancer, prostrate cancer, and breast cancer). Most compounds tested have shown very significant activity, with an average $GI_{50}$ ranging from 1.17 µM to 20.23 µM.

Based on the significant anti-cancer activity observed, several of the compounds belonging to various series mentioned above were tested for in vivo models such as, melanoma (UACC-257, UACC-262 and SK-MEL-28), Colon tumor(COLO 205 and KM20L2) and Murine Leukemia (P388). These compounds have shown significant activity in various in vivo models.

Because of their potent anti-inflammatory and anti-proliferative activities (in vitro cell lines) and anti-cancer activity (in Vitro and in vivo models), these novel compounds are useful anti-inflammatory, anti-proliferative and anti-cancer agents.

The compounds of the present invention may be prepared according to a general synthetic procedure. The examples mentioned below demonstrate the general synthetic procedure, as well as the specific preparation, for compounds according to this invention. The examples are illustrative, and are not intended to limit, in any manner, the claimed invention.

EXPERIMENTAL PROCEDURE

Various solvents, such as acetone, methanol, pyridine, ether, tetrahydrofuran, dimethylsulfoxide, hexanes, and ethylacetate were dried using various drying reagents by the procedure as described in the literature. Wet solvents gave poor yields of the products or intermediates. IR spectra were recorded as nujol mulls or a thin neat film on a Beckman Instrument using sodium chloride plates. PMR, CMR, and various 2D spectra were recorded on a Varian XL-300 MHz instrument using tetramethylsilane as an internal standard reference. CIMS were obtained on a Finnigan MAT-4510 mass spectrometer equipped with an INCOS data system. Generally, a direct exposure probe was used and methane was used as a reagent gas (0.35 mm Hg, 120° C. source temperature).

EXAMPLE 1

Preparation of 2,3-O-isopropylidene-1-O-dodecyl-6-deoxy-6-pyrrolidinyl-α-L-xylo-2-hexulofuranose (6, R=$C_{12}H_{25}$; $R_1$=pyrrolidinyl):

Step 1: 2,3:4,6-Di-O-isopropylidene-α-L-xylo-2- hexulofuranose (2)

2,3:4,6-Di-O-isopropylidene-α-L-xylo-2-hexulofuranosonic acid, a commercially available compound A (10 g) was dissolved in DMF (40 mL) and stirring started. To this was added 10 g of ethyl bromide and 5 g of anhydrous potassium carbonate. The reaction was stirred at ambient temperature for 8 hours and filtered. The solvents were removed and the residue extracted with ethyl acetate, washed with water, dried and solvent removed. A white solid (1) formed was recrystallized from ether, yield 94%.

CIMS: 303 (M+1).

The purified ethyl ester (1) formed above (10 g) was dissolved in 20 mL of tetrahydrofuran and added dropwise to a stirred solution of $LiAlH_4$ (2 equivalents) in THF (20 mL) at 5°–10° C., over a period of 15 minutes. The reaction mixture was further stirred for a period of 2 hours. The excess LAH was decomposed by the careful addition of 5 mL water followed by the addition of 5 mL of 3M sodium hydroxide solution. The reaction mixture was then filtered and washed with 100 mL of THF. The solvents were stripped off using rotary evaporator and the residue dissolved in ethylacetate (100 mL). The organic layer is washed with 2×20 mL water followed by washing with 1×20 mL of brine. The organic layer was then dried ($MgSO_4$), filtered, and solvent removed. A light yellow solid formed was recrystallized from ether to afford the title compound 2 in 85% yield, m.p- 114°–115° C.

CIMS: 261 (M+1).

Step 2: 2,3:4,6-Di-O-isopropylidene-α-L-xylo-1-O-dodecyl-2-hexulofuranose (3, R=$C_{12}H_{25}$)

General Procedure for the conversion of —OH group to —OR group:

Monosaccharide compound containing only one free OH group (5 g) is mixed with 2 equivalents of dry powdered sodium hydroxide or potassium hydroxide and 1.1 equivalents of suitable alkyl halide. The resulting mixture is heated in an oil bath, with stirring, at 90°–110° C. for 2–3 hours. Alternatively, the mixture is heated in a microwave oven at 50% power for 2–6 minutes. The progress of the reaction was followed by tlc. After the completion of the reaction, the reaction flask is cooled, added 50 ml of dichloromethane and stirred for 5 minutes. The resulting mixture was filtered through Celite and washed with 20 mL more of dichloromethane. The removal of the solvent gave the thick oil, which was purified by flash chromatography. The elution mixture normally used is ether:hexane (10:90) and the yield of the purified compound varies from 82–94%.

The title compound is prepared by the general procedure as described in step 2 above. The yield of the pure compound (3) was 91%.

CIMS: 429 (M+1).

Step 3: 2,3-O-Isopropylidene-1-O-dodecyl-α-L-xylo-2-hexulofuranose (4, R=$C_{12}H_{25}$)

Compound 3 obtained in step 2 (1 g) is dissolved in a mixture of one mL of THF and one mL water and cooled the solution at 5°–10° C. To this was added 1 mL of 30% perchloric acid dropwise with stirring. The progress of the reaction was followed by tlc. After one hour the reaction is quenched with a saturated solution of potassium carbonate (pH=9). The solid salt formed is filtered and washed with 10 mL of THF. The filtrate is subjected to rotovap to remove solvents. The residue was dissolved in ethyl acetate, washed with brine (2×20 mL), the organic layer dried ($MgSO_4$), filtered and solvent removed. The crude compound obtained is purified by column chromatography as a clear oil in 84% yield.

CIMS: 389 (M+1).

Step 4: 2,3-O-Isopropylidene-1-O-dodecyl-6-p-tosyl-α-L-xylo-2-hexulofuranose (4, R=$C_{12}H_{25}$)

To a solution of 2,3-O-Isopropylidene-1-O-dodecyl-α-L-xylo-2-hexulofuranose (4, R=$C_{12}H_{25}$) (12 g, 0.0309 mole) in pyridine (50 mL) was added a solution of p-toluenesulfonyl chloride (5.88 g; 0.0308 mole), dropwise, over a period of 10 minutes and keeping the temperature at 0°–5° C. After the complete addition of tosyl chloride, the reaction mixture was stirred for another 2 hours at the same temperature. After the completion of the reaction, solvents were removed under reduced pressure. The residue was dissolved in ethyl acetate (100 mL), washed with water (2×20 mL) followed by a washing with saturated solution of sodium bicarbonate (2×20 mL). The organic layer was dried ($MgSO_4$), filtered and solvent removed using rotovap. Solid formed was recrystallized from etherhexane. The yield of the pure compound was 93%.

CIMS: 543 (M+1).

Step 5: 2,3-O-isopropylidene-1-O-dodecyl-6-deoxy-6-pyrrolidinyl-α-L-xylo-2-hexulofuranose (6, R=$C_{12}H_{25}$; $R_1$=pyrrolidinyl)

A mixture of 2,3-O-Isopropylidene-1-O-dodecyl-6-p-tosyl-α-L-xylo-2-hexulofuranose (5, R=$C_{12}H_{25}$) (2 g) and pyrrolidine (2 mL) was heated on a oil bath at 70°–80° C. for 2 hours. The progress of the reaction was followed by tlc. Alternatively, this reaction was carried out in an microwave oven at 50% power and the reaction time was 4.2 minutes. The excess pyrrolidine was removed under reduced pressure and the residue dissolved in ethyl acetate (20 mL). The organic layer was then washed with a saturated solution of $NaHCO_3$ followed by washing with brine (2×10 mL). The ethyl acetate layer was dried with anhydrous $MgSO_4$, filtered, and solvent removed. The product was purified by flash chromatography and eluted with 30:70 mixture of ether:hexane. The yield of the pure product (viscous oil) was 88%.

CIMS: 442 (M+1).

EXAMPLE 2

Preparation of 2,3-O-Isopropylidene-6-deoxy-6-(1-piperidinyl)-1-O-dodecyl-α-L-xylo-2-hexulofuranose This compound was prepared by reacting compound 5 with piperidene by the same procedure as described in step 5 of example 1. The yield of the pure compound, purified by flash chromatography, was 88%.

CIMS: 456 (M+1).

EXAMPLE 3

Preparation of 2,3-O-Isopropylidene-6-deoxy-6-(1-morpholinyl)-1-O-dodecyl-α-L-xylo-2-hexulofuranose This compound was prepared by reacting compound 5 with morpholine by the same procedure as described in step 5 of example 1. The yield of the pure compound, purified by flash chromatography, was 89%

CIMS: 458 (M+1).

EXAMPLE 4

Preparation of 2,3-O-Isopropylidene-6-deoxy-6-(1-hexamethyleneimino)-1-O-dodecyl-α-L-xylo-2-hexulofuranose This compound was prepared by reacting compound 5 with hexamethyleneimine by the same procedure as described in step 5 of example 1. The yield of the pure compound, purified by flash chromatography, was 80%.

CIMS: 470 (M+1).

EXAMPLE 5

Preparation of 2,3-O-Isopropylidene-6-deoxy-6-aminoethylpyrrolidinyl)-1-O-dodecyl-α-L-xylo-2-hexulofuranose This compound was prepared by reacting compound 5 with N-(2-aminoethylpyrrolidine) by the same procedure as described in step 5 of example 1. The yield of the pure compound, purified by flash chromatography, was 83%.

CIMS: 485 (M+1).

EXAMPLE 6

Preparation of 2,3-O-Isopropylidene-6-deoxy-6-aminoethylmorpholinyl-1-O-dodecyl-α-L-xylo-2-hexulofuranose This compound was prepared by reacting compound 5 with N-(2-aminoethylmorpholine) by the same procedure as described in step 5 of example 1. The yield of the pure compound, purified by flash chromatography, was 87%.

CIMS: 501 (M+1).

EXAMPLE 7

Preparation of 2,3-O-Isopropylidene-6-deoxy-6-aminoethylpiperidine-1-O-dodecyl-α-L-xylo-2-hexulofuranose This compound was prepared by reacting compound 5 with N-(2-aminoethylpiperidene) by the same procedure as described in step 5 of example 1. The yield of the pure compound, purified by flash chromatography, was 80%.

CIMS: 499 (M+1).

EXAMPLE 8

Preparation of 2,3-O-Isopropylidene-6-deoxy-6-hexamethyleneiminoethyl-1-O-dodecyl-α-L-xylo-2-hexulofuranose This compound was prepared by reacting compound 5 with hexamethyleneiminoethyl by the same procedure as described in step 5 of example 1. The yield of the pure compound, purified by flash chromatography, was 91%.

CIMS: 513 (M+1).

EXAMPLE 9

Preparation of 2,3-O-Isopropylidene-6-deoxy-6-aminoethylcyclohexyl-1-O-dodecyl-α-L-xylo-2-hexulofuranose This compound was prepared by reacting compound 5 with N-(2-aminoethylcyclohexane) by the same procedure as described in step 5 of example 1. The yield of the pure compound, purified by flash chromatography, was 88%.

CIMS: 499 (M+1).

EXAMPLE 10

Preparation of 2,3-O-Isopropylidene-6-deoxy-6-phenylpropylamino-1-O-dodecyl-α-L-xylo-2-hexulofuranose This compound was prepared by reacting compound 5 with phenylpropylamine by the same procedure as described in step 5 of example 1. The yield of the pure compound, purified by flash chromatography, was 90%.

CIMS: 506 (M+1).

EXAMPLE 11

Preparation of 2,3-O-Isopropylidene-6-deoxy-6-hexamethyleneiminoethyl-1-O-dodecyl-4-O-phenylpropyl-α-L-xylo-2-hexulofuranose 2,3-O-Isopropylidene-6-deoxy-6-hexamethyleneiminoethyl-1-O-dodecyl-α-L-xylo-2-hexulofuranose (2 g) was treated with dry, powdered sodium hydroxide and 1-bromo-3-phenylpropane by the same procedure as described in step 2 of example 1. The yield of the trisubstituted compound was 77%, after purification by flash chromatography.

CIMS: 588 (M+1).

EXAMPLE 12

Preparation of 2,3-O-Isopropylidene-6-deoxy-1-O-dodecyl-5-O-ethylpyrrolidinyl-α-L-xylo-2-hexulofuranose Step 1: 2,3-O-Isopropylidene-6-deoxy-1-O-dodecyl-α-L-xylo-2-hexulofuranose (7, R=$C_{12}H_{25}$)

The compound 5 (10.84 g; 0.02 moles) was dissolved in 100 mL of dry tetrahydrofuran and added dropwise to a stirred suspension of lithium aluminium hydride (0.912 g; 0.024 moles) in 50 mL of THF at 0°–5° C., over a period of 10 minutes. The reaction mixture was stirred at the same temperature for 3 hours. The progress of the reaction was monitored by tlc. The excess $LiAlH_4$ was decomposed by careful addition of 1 mL water followed by the addition of 1 mL of 3N NaOH solution. The reaction mixture was filtered through Celite, washed with 100 mL THF and the solvents removed under rotovap. The residue was dissolved in 100 mL ether and washed with 20 mL brine. The organic layer dried ($MgSO_4$), filtered and solvent removed. The colorless oil (7 g) showed a single spot on tlc and hence used as such for the next step.

CIMS: 373 (M+1).

Step 2: 2,3-O-Isopropylidene-6-deoxy-1-O-dodecyl-4-O-ethylpyrrolidinyl-α-L-xylo-2-hexulofuranose

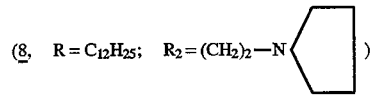

(8, R = $C_{12}H_{25}$; $R_2$ = $(CH_2)_2$—N⟨ ⟩)

2,3-O-Isopropylidene-6-deoxy-1-O-dodecyl-α-L-xylo-2-hexulofuranose (3.72 g; 0.01 mole) was heated in an oil bath with 0.8 g of powdered sodium hydroxide and 1.2 equivalents of 1-(2-chloroethyl) pyrrolidine at 80°–100° C. for 2 hours or in a microwave oven for 6.2 minutes at 50% power. The reaction mixture was cooled and added 50 mL of ether. The solid salts formed was filtered and the filtrate subjected to rotovap. The light yellow oil formed was purified by flash chromatography using silica gel and eluting with 10:90 mixture of ether:hexane. The yield of the pure compound was 4.32 g (90.1%).

CIMS: 470 (M+1).

Other compounds which were prepared similarly, as described in Example 12, were as follows:

2,3-O-Isopropylidene-6-deoxy-1-O-dodecyl-4-O-ethylpiperidinyl-α-L-xylo-2-hexulofuranose.

2,3-O-Isopropylidene-6-deoxy-1-O-dodecyl-4-O-ethylmorpholinyl-α-L-xylo-2-hexulofuranose.

2,3-O-Isopropylidene-6-deoxy-1-O-dodecyl-4-O-ethylhexamethyleneimino-α-L-xylo-2-hexulofuranose.

2,3-O-Isopropylidene-6-deoxy-1-O-dodecyl-4-O-phenylpropyl-α-L-xylo-2-hexulofuranose.

2,3-O-Isopropylidene-6-deoxy-1-O-dodecyl-4-O-3'-(N,'N'-dimethylaminopropyl)-α-L-xylo-2-hexulofuranose.

EXAMPLE 13

Preparation of 2,3-O-Isopropylidene-6-deoxy-1-O-dodecyl-4-O-ethylpyrrolidinyl-6-hexamethyleneimino-α-L-xylo-2-hexulofuranose (9, R = $C_{12}H_{25}$; $R_1$ = hexamethyleneimino;

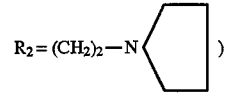

$R_2$ = $(CH_2)_2$—N⟨ ⟩)

2,3-O-Isopropylidene-6-deoxy-6-(1-hexamethyleneimino)-1-O-dodecyl-α-L-xylo-2-hexulofuranose (2 g) as prepared in example 4 was treated with NaOH and 1-(2-chloroethyl)pyrrolidine by the same procedure as described in step 2 of example 12. The only difference was that the reaction time varied from 5–6 hours. The yield of the purified compound (flash chromatography) was 86%.

CIMS: 553 (M+1).

Other compounds which were prepared similarly, as described in Example 13, were as follows:

2,3-O-Isopropylidene-6-deoxy-1-O-dodecyl-4-O-propylpyrrolidinyl-6-hexamethyleneimino-α-L-xylo-2-hexulofuranose 2,3-O-Isopropylidene-6-deoxy-1-O-dodecyl-4-O-ethylpiperidinyl-6-hexamethyleneimino-α-L-xylo-2-hexulofuranose 2,3-O-Isopropylidene-6-deoxy-1-O-dodecyl-4-O-propylpiperidinyl-6-hexamethyleneimino-α-L-xylo-2-hexulofuranose 2,3-O-Isopropylidene-6-deoxy-1-O-dodecyl-4-O-ethylmorpholinyl-6-hexamethyleneimino-α-L-xylo-2-hexulofuranose 2,3-O-Isopropylidene-6-deoxy-1-O-dodecyl-4-O-phenylpropyl-6-hexamethyleneimino-α-L-xylo-2-hexulofuranose 2,3-O-Isopropylidene-6-deoxy-1-O-dodecyl-4-O-3'-(N',N'-dimethylaminopropyl)-6-hexamethyleneimino-α-L-xylo-2-hexulofuranose

PHARMACOLOGICAL ACTIVITY

The compounds of the present invention have demonstrated immunomodulatory and anti-inflammatory effects in biological assays. Various standard in vitro assays have been performed on most of the compounds of the present invention to ascertain immunomodulatory and anti-proliferative activities. These include:

i Mixed lymphocyte response (MLR).

ii BUD-8 human cell line fibroblast proliferation assay.
iii Concanavalin A assay (the mouse spleen cell mitogen induced blastogenesis).

The MLR assay measures the effects of a study compound on the activation and antigen presentation of T-lymphocytes, therefore determining immunomodulatory properties. The mouse spleen cell mitogen-induced blastogenesis and the BUD-8 human fibroblast proliferation assays measure the effects of the the compounds of the present invention on cellular proliferation of cells involved in the pathogenesis of autoimmune diseases. These two assays are appropriate as screens to ascertain anti-inflammatory and/or autoimmune diseases.

The MLR is a classical assay used to measure T cell function by studying the proliferation response of T cells which are activated in vitro by genetically disparate stimulator cells. This is accomplished by co-culturing spleen cells from two different strains of mice. Splenic T cell proliferation occurs as a result of cellular activation signals generated by the ongoing cellular interactions.

A second assay was conducted to demonstrate inhibitory activity of the compounds of the present invention to the in vitro proliferation of human skin cells in tissue culture. The skin cell fibroblast line, BUD-8, was originally derived from the normal skin of a 56 year old white female and can now be obtained from the American Type Culture Collection, Rockville, Md.

A third assay was conducted to demonstrate the ability of the compounds of the present invention to modulate T-lymphocyte activity. It is known that the induction and maintenance of most inflammatory diseases are typically due to the unrestricted activity of T-lymphocytes. Therefore, it is advantageous to identify compounds which are modulators of T-lymphocyte activity for eventual use in the regulation of inflammatory diseases, including acquired immune deficiency syndrome, psoriasis, systemic lupus, erythromatosus, and rheumatoid arthritis.

The detailed experimental procedure for the above-mentioned assays is described in detail in U.S. Pat. Nos. 5,360,790 and 5,367,062 incorporated herein by reference.

The compounds of the present invention were also tested against various tumor cell lines, derived from ten cancer types. These include leukemia, melanoma, lung cancer, colon cancer, renal cancer, ovarian cancer, brain cancer, breast cancer and prostate cancer. A total of 60–69 cancer cell lines were used. Most of the compounds have shown significant activity in various screens.

Most of the compounds of the present invention were tested (in vitro) in the National Cancer Institute's in vitro disease oriented antitumor screen, which determines a test agent's effect on growth parameters against a panel of more than 60 human tumor cell lines (Monks, A. et. al., Feasibility of a High Flux Anticancer Drug Screen Utilizing a Derive Panel of Human Tumor Cell Lines in Culture, J. Natl. Cancer Inst. 1991, 83, 757–766; Boyd, M. R., Status of the NCI Preclinical Antitumor Drug Discovery Screen. *In Cancer: Principles and Practice of Oncology Updates;* De Vita et. al., Eds.; J. B. Lippincott: Philadelphia, 1989; pp 1–12.).

In performing in vitro human tumor cell line assay, a total of approximately 60 human tumor cell lines derived from ten cancer types (leukemia, non-small cell lung cancer, small cell lung cancer, colon cancer, CNS cancer, melanoma, ovarian cancer, renal cancer, breast cancer and prostate cancer) were used in this assay. Compounds were tested at different concentrations against every cell line. All lines are inoculated into a series of standard 96-well microtiter plates on day 0, in the majority of cases at 20,000 cells/well, and then pre-incubated in the absence of testing agent for 24 hours. A testing agent was then added in five 10-fold dilutions and incubated for a further period of 48 hours. Following this, the cells are fixed in situ, washed, and dried. Sulforhodamine B (SRB, protein binding dye) is added, followed by further washing and drying of the stained adherent cell mass. The bound stain is solubilized and measured spectrophotometrically on an automatic plate reader.

For each compound, dose response curves for each cell line were measured with five different drug concentrations, and the concentration causing 50% cell growth inhibition ($GI_{50}$), total cell growth inhibition (TGI, 0% growth), and 50% cell death ($LC_{50}$, −50% growth) compared with the control was calculated. The $\log_{10} GI_{50}$ of compounds tested are expressed in the form of mean graph (compound Ie is illustrated in FIG. 1). In these graphs, the mean logarithmic value of $GI_{50}$ in all cell lines for each tested compound is used as the midpoint of that bar graph. Bars extending to the right represent sensitivity of the cell line to the test agent in excess of the average sensitivity of all tested cell lines. The bar scale is logarithimic; therefore, a bar 2 units to the right shows the compound achieved the $GI_{50}$ for the cell line at a concentration one-hundredth the mean concentration required over all cell lines; thus the cell line is unusually sensitive to the compound. Bars extending to the left correspondly imply sensitivity less than the mean. The $\log_{10}$ TGI and $\log_{10} LC_{50}$ values for all the compounds tested were also measured and can be expressed with similar bar mean graphs; however, only the mean graph midpoint values of $\log_{10}$ TGI and $\log_{10} LC_{50}$, as well as $\log_{10} GI_{50}$ are listed in Table 1.

TABLE 1

$IC_{50}$ (MLR, CON-A, FIBROBLAST), $\log_{10} GI_{50}$, $GI_{50}$ (μM), $\log_{10}$ TGI, and $\log_{10} LC_{50}$ Mean Graph Midpoints (MG_MID) of in vitro Inhibitory Activity Tests for Compounds against MLR, CON-A, FIB. and Human Tumor Cell Lines

| | Anti-inflammatory/ Anti-proliferative Activity | | | Antitumor Activity (Average) | | | |
|---|---|---|---|---|---|---|---|
| | $IC_{50}$ (μM) | | | $GI_{50}$ | | | |
| COMPOUND # | MLR | CON-A | FIB. | $\log_{10} I_{50}$ | μM | $\log_{10}$ TGI | $\log_{10} LC_{50}$ |
| Ic | <1 | 10.3 | 14.8 | −4.84 | 31.62 | −4.53 | −4.25 |
| Id | <1 | <3 | <3 | −5.74 | 3.87 | −5.34 | −4.97 |

TABLE 1-continued

IC$_{50}$ (MLR, CON-A, FIBROBLAST), log$_{10}$ GI$_{50}$, GI$_{50}$ (μM),
log$_{10}$ TGI, and log$_{10}$ LC$_{50}$ Mean Graph Midpoints (MG_MID) of in
vitro Inhibitory Activity Tests for Compounds against MLR,
CON-A, FIB. and Human Tumor Cell Lines

| COMPOUND # | Anti-inflammatory/ Anti-proliferative Activity IC$_{50}$ (μM) | | | Antitumor Activity (Average) | | | |
|---|---|---|---|---|---|---|---|
| | MLR | CON-A | FIB. | log$_{10}$ I$_{50}$ | GI$_{50}$ μM | log$_{10}$ TGI | log$_{10}$ LC$_{50}$ |
| Ia | <1 | <1 | <3 | −6.69 | 4.21 | −5.36 | −4.88 |
| If | <1 | <1 | <1 | −5.63 | 4.68 | −5.29 | −4.96 |
| Ig | <1 | <3 | <3 | −5.47 | 6.80 | −5.11 | −4.70 |
| Il | <1 | <1 | <1 | −5.39 | 8.68 | −4.98 | −4.54 |
| Im | <1 | 7.4 | 3.6 | −5.01 | 20.23 | −4.64 | −4.30 |
| In | 3.8 | 10.5 | 12.9 | −4.44 | 74.86 | −4.14 | −4.04 |
| Ir | <1 | <1 | <1 | −5.75 | 3.22 | −5.09 | −4.67 |
| It | <1 | <1 | <1 | −5.87 | 2.38 | −5.11 | −4.44 |
| Iu | <1 | <1 | <1 | −6.30 | 0.86 | −5.43 | −4.54 |
| Iv | <1 | <1 | <1 | −5.74 | 3.20 | −4.94 | −4.35 |
| Iw | <1 | <1 | <1 | −5.61 | 4.18 | −5.00 | −4.78 |

IC$_{50}$: Effective molar concentration at 50% inhibition. GI$_{50}$: Drug molar concentration causing 50% cell growth inhibition. TGI: Drug concentration causing total cell growth inhibition (0% growth). LC$_{50}$: Drug concentration causing 50% cell death (−50% growth). MG_MID: Mean graph midpoints, the average sensitivity of all cell lines toward the test agent.

As demonstrated by the IC$_{50}$, average GI$_{50}$, and mean graph pattern, these compounds have shown highly significant activity against various in vitro cell lines. Therefore, these compounds can be effectively useful for treating various animals and mammals with inflammatory and or autoimmune disorders as well as for treating various cancer diseases. From the above results, it is clear that trisubstituted compounds (Ir–Ix) are highly effective followed by the compounds represented by scheme 1 (Id–Ig). The compounds of scheme 2 have also shown significant activity (II), but they were less potent than other two series.

Based on the significant in vitro activity, two of the compounds were also tested for in vivo models for treating various cancers. A brief summary of various compounds tested in various in vivo models is described:

Response of Early Stage Subcutaneous Tumor Model UACC-62 Melanoma Xenografts to compound Ic. and Im Two of the compounds, which have shown significant activity in various in vitro cell lines (Ic and Im), were selected for Early stage subcutaneous tumor model.

In this in vivo model Murine or human tumor fragments (30 mg) are implanted subcutaneously into the axillary region of pathogen-free immunocompetent or immunodeficient mice, respectively, on experimental day 0. Test agent treatment is initiated either on the day which is historically associated with the start of tumor growth, or when the tumor is palpable. Tumor size and body weights are obtained approximately two times per week. Tumor weights are calculated from caliper measurements of tumor dimensions in mm using the formula for a prolate ellipsoid:

$$(L \times W^2)/2;\ \text{where L is the longer of the 2 measurements}$$

Generally, tumor size is monitored until an upper weight limit of 500 mg is attained.

In the present case, mice with tumor was treated with compound Ic, 2,3-O-Isopropylidene-6-deoxy-6-(1-morpholinyl)-1-O-dodecyl-α-L-xylo-2-hexulofuranose and Im, 2,3-O-Isopropylidene-6-deoxy-1-O-dodecyl-4-O-ethylpiperidinyl-α-L-xylo-2-hexulofuranose, to supress the tumor growth. The details of the test performed is as follows:

| Grp. # | Compd. # | Dose/units | Route | Schedule | No. of Mice | Drug Deaths | Net wt. Loss (day) | Opt. % T/C (day) |
|---|---|---|---|---|---|---|---|---|
| Resonse of Early Stage Subcutaneous Tumor Model UACC-62 Melanoma Xenografts to compound Ic. and Im: | | | | | | | | |
| 1 | control | 0 mg/kg/dose | IP | Q4D × 3, day 6 | 20 | 0 | 20.7 (23) | |
| 2. | Ic | 200 mg/kg/dose | IP | Q4D × 3, day 6 | 6 | 6 | no wt. loss | Toxic |
| 3. | Ic | 134 mg/kg/dose | IP | Q4D × 3, day 6 | 6 | 6 | 10.5 (9) | Toxic |
| 4. | Ic | 90 mg/kg/dose | IP | Q4D × 3, day 6 | 6 | 0 | 27.3 (23) | 39 (16) |
| 5. | Im | 130 mg/kg/dose | IP | Q4D × 3, day 6 | 6 | 1 | 3.2 (9) | 42 (16) |
| 6. | Im | 90 mg/kg/dose | IP | Q4D × 3, day 6 | 6 | 0 | no wt. loss | 44 (16) |
| 7. | Im | 54 mg/kg/dose | IP | Q4D × 3, day 6 | 6 | 0 | 4.4 (23) | 51 (9) |
| Response of Early Stage SK-MEL-28 Melanoma Xenografts to Compounds Ic and Im: | | | | | | | | |
| 1 | control | 0 mg/kg/dose | IP | QD × 5, day 3 | 20 | 0 | no wt. loss | |
| 2. | Ic | 200 mg/kg/dose | IP | QD × 5, day 3 | 6 | 6 | 2.3 (6) | Toxic |
| 3. | Ic | 134 mg/kg/dose | IP | QD × 5, day 3 | 6 | 1 | 1.2 (9) | 36 (9) |
| 4. | Ic | 90 mg/kg/dose | IP | QD × 5, day 3 | 6 | 0 | 1.5 (9) | 35 (16) |
| 5. | Im | 130 mg/kg/dose | IP | QD × 5, day 3 | 6 | 5 | 5.4 (6) | Toxic |

-continued

| Grp. # | Compd. # | Dose/units | Route | Schedule | No. of Mice | Drug Deaths | Net wt. Loss (day) | Opt. % T/C (day) |
|---|---|---|---|---|---|---|---|---|
| 6. | Im | 90 mg/kg/dose | IP | QD × 5, day 3 | 6 | 2 | 4.0 (9) | 49 (9) |
| 7. | Im | 54 mg/kg/dose | IP | QD × 5, day 3 | 6 | 1 | 3.5 (9) | 47 (16) |
| | | Response of Early Stage SC COLO 205 Colon Tumor Xenografts to Compounds Ic and Im: | | | | | | |
| 1 | control | 0 mg/kg/dose | IP | Q4D × 3, day 7 | 20 | 0 | 1.1 (16) | |
| 2. | Ic | 200 mg/kg/dose | IP | Q4D × 3, day 7 | 6 | 6 | 13.6 (10) | Toxic |
| 3. | Ic | 134 mg/kg/dose | IP | Q4D × 3, day 7 | 6 | 1 | 11.1 (16) | 40 (29) |
| 4. | Ic | 90 mg/kg/dose | IP | Q4D × 3, day 7 | 6 | 0 | 2.6 (20) | 43 (36) |
| 5. | Im | 130 mg/kg/dose | IP | Q4D × 3, day 7 | 6 | 4 | 17.2 (10) | Toxic |
| 6. | Im | 90 mg/kg/dose | IP | Q4D × 3, day 7 | 6 | 0 | 4.8 (16) | 45 (29) |
| 7. | Im | 54 mg/kg/dose | IP | Q4D × 3, day 7 | 6 | 0 | 2.0 (20) | 44 (36) |

These compounds were evaluated at a maximally tolerated dose. IP = Intraperitoneal; The schedule is shown in abbreviated form, wherein Q4D × 3, day 6 represents every four days for a total of 3 treatments with the first treatment given on day 6; Opt. % T/C (day) represents percent treated/control and is calculated by dividing the median treated tumor weight by median control weight on each observation day and multiplying by 100. This calculation is performed each day the tumors are measured and the optimum value (minimum), obtained after the first course of treatment, is presented. The day on which this optimum T/C occurs is shown in parenthesis. A T/C % of greater than 40 is considered inactive). The control group received 0.1 ml/10 g body weight of a solution of saline + Tween 80 (0.05%). Similarly, the sample solutions were also prepared in saline and Tween 80 (0.05%) and were injected at the same volume as the control group.

Response of P388 Murine Leukemia to compound Ic and Im

Two of the compounds of the present invention (Ic and Im) were also tested against P388 Murine Leukemia. Three doses were used for each compound (60, 40 and 27 mg/kg/dose for compound Ic and 120, 80, and 54 mg/kg/dose for compound Im). Both of these compounds were toxic at the higher dose levels. Both of these compounds have shown only slight antitumor activity on the treatment evaluated in the present study. However, a maximally tolerated dose was not achieved for both of these compounds.

While the present invention has been described in terms of its specific embodiments, certain modifications and equivalents will be apparent to those skilled in art and are intended to be included within the scope of the present invention, which is to be limited only by scope of the appended claims.

What is claimed as new and desired to be secured by Letters Patent of the United States is:

1. A compound of formula I

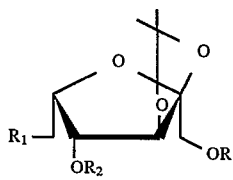

wherein

R is $C_{10}-C_{15}$ alkyl;

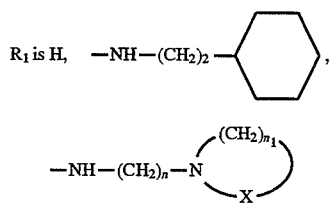

wherein x is O or $CH_2$ and n and $n_1$ are from 2–6 or

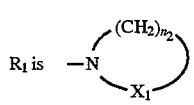

wherein $X_1$ is O or $CH_2$ and $n_2$ is 2–6;

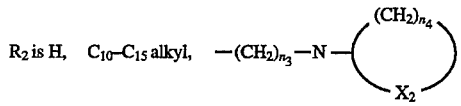

wherein $X_2$ is O or $CH_2$ and $n_3$ and $n_4$ are from 2–6, or $R_2$ is $-(CH_2)_{n_5}-N(CH_3)_2$ wherein $n_5$ is from 2–4 or a pharmaceutically acceptable salt thereof.

2. A compound according to claim 1, selected from the group consisting of:

2,3-O-Isopropylidene-6-deoxy-6-(1-pyrrolidinyl)-1-O-dodecyl-α-L-xylo-2-hexulofuranose, 2,3-O-Isopropylidene-6-deoxy-6-(1-piperidinyl)-1-O-dodecyl-α-L-xylo-2-hexulofuranose, 2,3-O-Isopropylidene-6-deoxy-6-(1-morpholinyl)-1-O-dodecyl-α-L-xylo-2-hexulofuranose, 2,3-O-Isopropylidene-6-deoxy-6-(1-hexamethyleneimino)-1-O-dodecyl-α-L-xylo-2-hexulofuranose, 2,3-O-Isopropylidene-6-deoxy-6-aminoethylpyrrolidinyl)-1-O-dodecyl-α-L-xylo-2-hexulofuranose, 2,3-O-Isopropylidene-6-deoxy-6-aminoethylmorpholinyl-1-O-dodecyl-α-L-xylo-2-hexulofuranose, 2,3-O-Isopropylidene-6-deoxy-6-aminoethylpiperidinyl-1-O-dodecyl-α-L-xylo-2-hexulofuranose, 2,3-O-Isopropylidene-6-deoxy-6-aminoethylhexamethyleneimino-1-O-dodecyl-α-L-xylo-2-hexulofuranose, 2,3-O-Isopropylidene-6-deoxy-6-aminopropylpyrrolidinyl-1-O-dodecyl-α-L-xylo-2-hexulofuranose, 2,3-O-Isopropylidene-6-deoxy-6-aminoethylcyclohexyl-1-O-dodecyl-α-L-xylo-2-hexulofuranose, 2,3-O-Isopropylidene-6-deoxy-6-phenylpropylamino-1-O-dodecyl-α-L-xylo-2-hexulofuranose, 2,3-O-Isopropylidene-6-deoxy-1-O-dodecyl-4-O-ethylpyrrolidinyl-α-L-xylo-2-hexulofuranose, 2,3-O-Isopropylidene-6-deoxy-1-O-dodecyl-4-O-ethylpiperidinyl-α-L-xylo-2-hexulofuranose, 2,3-O-Isopropylidene-6-deoxy-1-O-dodecyl-4-O-ethylmorpholinyl-α-L-xylo-2-hexulofuranose, 2,3-O-Isopropylidene-6-deoxy-1-O-dodecyl-4-O-ethylhexamethyleneimino-α-L-xylo-2-hexulofuranose, 2,3-O-Isopropylidene-6-deoxy-1-O-dodecyl-4-O-phenylpropyl-α-L-xylo-2-hexulofuranose, 2,3-O-Isopropylidene-6-deoxy-1-O-dodecyl-4-O-3'-(N',N'-dimethylaminopropyl)-α-L-xylo-2-hexulofuranose, 2,3-O-Isopropylidene-6-deoxy-1-O-dodecyl-4-O-ethylpyrrolidinyl-6-hexamethyleneimino-α-L-xylo-2-hexulofuranose, 2,3-O-Isopropylidene-6-deoxy-1-O-dodecyl-4-O-propylpyrrolidinyl-6-hexamethyleneimino-α-L-xylo-2-hexulofuranose, 2,3-O-Isopropylidene-6-deoxy-1-O-dodecyl-4-O-ethylpiperidinyl-6-hexamethyleneimino-α-L-xylo-2-hexulofuranose, 2,3-O-Isopropylidene-6-deoxy-1-O-dodecyl-4-O-propylpiperidinyl-6-hexamethyleneimino-α-L-xylo-2-hexulofuranose, 2,3-O-Isopropylidene-6-deoxy-1-O-dodecyl-4-O-ethylmorpholinyl-6-hexamethyleneimino-α-L-xylo-2-hexulofuranose, 2,3-O-Isopropylidene-6-deoxy-1-O-dodecyl-4-O-phenylpropyl-6-hexamethyleneimino-α-L-xylo-2-hexulofuranose, and 2,3-O-Isopropylidene-6-deoxy-1-O-dodecyl-4-O-3'-(N',N'-dimethylaminopropyl)-6-hexamethyleneimino-α-L-xylo-2-hexulofuranose.

3. A pharmaceutical composition comprising a pharmaceutically effective amount of a compound according to claim 1 and a pharmaceutically acceptable carrier.

4. A method of treating an animal or human suffering from an autoimmune disorder comprising administering thereto an amount of a compound according to claim 1 effective to treat the autoimmune disorder.

5. The method of claim 4, wherein said administration is oral administration.

6. The method of claim 4, wherein said administration is parenteral administration.

7. A method of treating an animal or human suffering from cancer comprising administering thereto an amount of a compound according to claim 1 effective to treat said cancer wherein the cancer is Leukemia, non-small cell lung cancer, colon cancer, CNS cancer, melanoma, ovarian cancer, renal cancer, prostrate cancer, or breast cancer.

8. The method of claim 7, wherein said administration is oral administration.

9. The method of claim 7, wherein said administration is parenteral administration.

10. The composition as claimed in claim 3, comprising 1–50 mg of said compound.

* * * * *